(12) United States Patent
Schaller et al.

(10) Patent No.: US 9,326,807 B2
(45) Date of Patent: May 3, 2016

(54) PERI-PROSTHETIC FIXATION IMPLANT AND METHOD

(75) Inventors: Konrad Schaller, Grenchen (CH); Tom Overes, Langendorf (CH); Robert Frigg, Bettlach (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1406 days.

(21) Appl. No.: 12/767,245

(22) Filed: Apr. 26, 2010

(65) Prior Publication Data

US 2010/0298829 A1 Nov. 25, 2010

Related U.S. Application Data

(60) Provisional application No. 61/179,881, filed on May 20, 2009.

(51) Int. Cl.
*A61B 17/82* (2006.01)
*A61B 17/88* (2006.01)
*A61B 17/80* (2006.01)
*A61B 17/00* (2006.01)
*A61F 2/36* (2006.01)

(52) U.S. Cl.
CPC .............. *A61B 17/8861* (2013.01); *A61B 17/82* (2013.01); *A61B 17/80* (2013.01); *A61B 2017/00867* (2013.01); *A61F 2/36* (2013.01)

(58) Field of Classification Search
CPC ............................................ A61B 2017/00867
USPC ..................................... 606/74, 103, 148, 139
See application file for complete search history.

(56) References Cited

U.S. PATENT DOCUMENTS

| | | | |
|---|---|---|---|
| 3,311,110 A * | 3/1967 | Sol Singerman et al. ...... | 606/226 |
| 3,570,497 A * | 3/1971 | Lemole .......................... | 606/151 |
| 4,535,764 A * | 8/1985 | Ebert .............................. | 606/74 |
| 4,643,178 A * | 2/1987 | Nastari et al. .................. | 606/74 |
| 4,730,615 A * | 3/1988 | Sutherland et al. ............ | 606/215 |
| 5,089,012 A * | 2/1992 | Prou .............................. | 606/224 |
| 5,250,055 A * | 10/1993 | Moore et al. ................... | 606/148 |
| 5,318,566 A * | 6/1994 | Miller ............................ | 606/60 |
| 5,366,461 A * | 11/1994 | Blasnik .......................... | 606/151 |
| 5,417,690 A * | 5/1995 | Sennett et al. ................. | 606/74 |
| 5,437,685 A * | 8/1995 | Blasnik .......................... | 606/151 |
| 5,536,270 A * | 7/1996 | Songer et al. .................. | 606/74 |
| 5,741,260 A * | 4/1998 | Songer et al. .................. | 606/74 |
| 5,766,218 A * | 6/1998 | Arnott ............................ | 606/151 |
| 2003/0009177 A1* | 1/2003 | Middleman et al. ........... | 606/127 |
| 2003/0083695 A1 | 5/2003 | Morris et al. | |
| 2006/0258951 A1 | 11/2006 | Bleich et al. | |

* cited by examiner

*Primary Examiner* — Zade Coley
(74) *Attorney, Agent, or Firm* — Fay Kaplun & Marcin, LLP

(57) ABSTRACT

An apparatus for leading a cerclage member along a desired path through a portion of bone, comprises a guide strip extending from a proximal end to a sharpened distal end, at least a portion of the guide strip being biased to assume a shape corresponding to a portion of a desired path along which the cerclage member is to pass through a portion of bone and a delivery cannula including a lumen sized to slidably receive the guide strip therein, the cannula maintaining the guide strip in a substantially straight configuration until the guide strip is extended distally out of the lumen.

15 Claims, 4 Drawing Sheets

PERI-PROSTHETIC FIXATION IMPLANT AND METHOD

PRIORITY CLAIM

The present application claims priority to U.S. Provisional Application Ser. No. 61/179,881 entitled "Peri-Prosthetic Fixation Implant and Method" filed on May 20, 2009 to Konrad Schaller, Tom Overes and Robert Frigg, the entire disclosure of which is incorporated herein by reference.

BACKGROUND

Fractures are often treated by wrapping a wire or other cable around a target portion of bone to stabilize the bone. The cable is typically looped around the target bone and locked at a desired tension therearound to hold portions of bone in a desired spatial relation to one another. Known cables for this purpose are generally formed with bulky heads that lockingly engage elongated portions thereof to maintain the cable looped around a target portion of bone with a desired tension. However, the large profile of these locking heads often requires that they project away from the bone and associated medical device (e.g., bone screw, bone plate, etc.) irritating ligaments, nerves and other adjacent tissue. Furthermore, once implanted, such cables often loosen and slide along an outer perimeter of the bone reducing the mechanical stability of the treated bone and increasing the possibility of further fractures. Bone defects such as osteoporosis further increase the likelihood of such fractures. Such loosening and movement of a cable may also result in misalignment, stiffness, nonunion, abnormal joint mechanics, healing impairment, etc

SUMMARY OF THE INVENTION

The present invention is directed to an apparatus for leading a cerclage member along a desired path through a portion of bone, comprising a guide strip extending from a proximal end to a sharpened distal end, at least a portion of the guide strip being biased to assume a shape corresponding to a portion of a desired path along which the cerclage member is to pass through a portion of bone in combination with a delivery cannula including a lumen sized to slidably receive the guide strip therein, the cannula maintaining the guide strip in a substantially straight configuration until the guide strip is extended distally out of the lumen.

DETAILED DESCRIPTION

Figure 1:
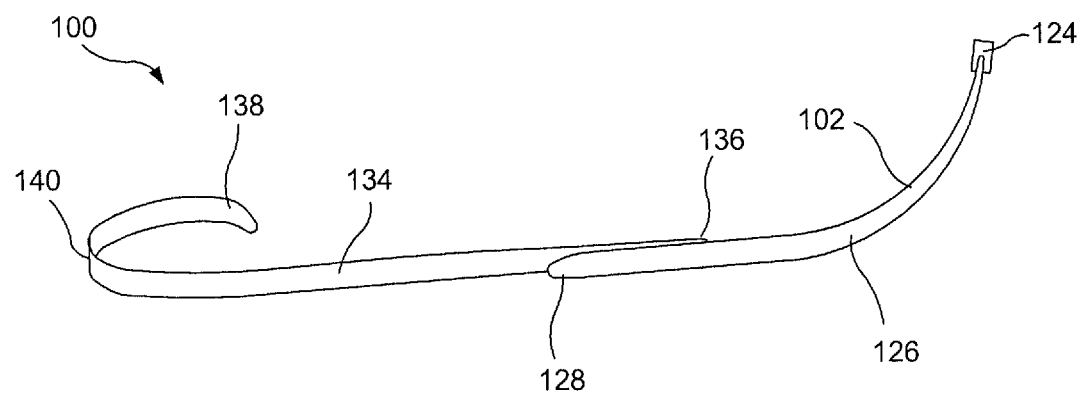
FIG. 1 shows a first perspective view of a system according to a first embodiment of the present invention.

The present invention may be further understood with reference to the following description and the appended drawings, wherein like elements are referred to with the same reference numerals. The present invention relates generally to methods and devices for the stabilization and fixation of fractured bones and bone fragments via cerclage. Specifically, the present invention relates to a cable tie that is configured to lock the cable in a desired position about a target bone, with dimensions of the cable tie being selected to minimize or prevent the irritation of adjacent tissues. An exemplary cable tie according to the present invention is formed with self-locking notches formed on a body thereof to permit the cable tie to lock in place when positioned around a target portion of bone. In an exemplary method of use, a cable including a cable tie according to the present invention may be passed through a portion of the target bone via a first hole predrilled into a portion of the target bone, around a periphery of a previously implanted bone fixation device and out of the bone via a second predrilled hole substantially parallel to the first hole. A distal portion of the cable may be formed to assume a predefined shape corresponding to a path along which it is to travel around the implanted bone fixation device from the first hole to the second hole with a distal end thereof sharpened to facilitate the penetration of intervening bone. The distal end may then be inserted into a head of the cable tie so that a first locking feature of the distal end of the cable lockingly engages a corresponding second locking feature of the head to lock the cable at a desired tension around the bone fixation device and a portion of bone between external openings of the first and second holes (i.e., openings to these holes at the surface of the bone). Embodiments of the present invention may be employed with any of a plurality of procedures involving cerclage including peri-prosthetic bone fixation procedures and trolley spine procedures, as those skilled in the art will understand. It is noted that although embodiments of the present invention are directed to the treatment of long bones, the exemplary system and method can be applied to any bone fixation procedure without deviating from the spirit and scope of the present invention. As used in this application, the terms proximal and distal refer to directions along the cable tie with a distal end including the sharpened tip which forms the leading end of the cable as it is inserted into the bone. The cable extends proximally from this end.

As shown in FIGS. 1-6, a system 100 and method according to a first embodiment of the invention include a cable tie 102 configured for insertion through a portion of bone to anchor a bone plate 104 or other item at a desired position on a bone 112. The cable tie 102 is formed with a longitudinal section 126 extending distally from a head 124 at a proximal end thereof to a distal end 128. The longitudinal section 126 includes a ribbed portion (not shown) configured to engage a tab (not shown) formed in the head 124, as those skilled in the art will understand. A length of the cable tie 102 is chosen, for example, from any of a plurality of standard lengths known in the art and appropriate for a procedure to be performed. The cable tie 102 may be formed of any flexible yet durable material including, but not limited to, a compound plastic, polyaryletheretherketone ("PEEK"), or any other biocompatible plastic wherein the selected material may, for example, be chosen based on the expected load to be applied thereto during and after insertion to a target portion of bone. In a first operative configuration, the distal end 128 of the cable tie 102 is temporarily attached to a proximal end 136 of a guide strip 134. The guide strip 134 extends from the proximal end 136 to sharpened distal end 138. A predetermined length of the distal end of the guide strip 134 is biased to assume a preformed curvature corresponding to a desired path of the cable tie 102 through a portion of the bone 112, as will be described in greater detail hereinafter. The guide strip 134 may be formed, for example, of Nitinol which has shape-memorizing properties permitting memorization of the predetermined curvature 340 or any other suitable material, as those skilled in the art will understand.

FIGS. 2-6 sequentially depict the process by which the system 100 and guide strip 134 may be used to lock the bone plate 104 to the target bone. The bone 112 may, for example, be a fractured long bone or any other bone in a living body. Those skilled in the art will understand that, in some cases or locations, the use of bone screws may not be desirable due to potential interference with a previously inserted bone fixation device such as a stem, rod or shaft 108. In addition, cables used to anchor fixation devices (e.g., bone plates) on long bones may sometimes slide along the bone away from a desired position. The following exemplary method permits the attachment of a bone fixation device such as a bone plate 104 to the bone 112 using a cable tie inserted through the bone 112 around a periphery of a shaft 108 of a previously inserted bone fixation device. The bone plate 104 may be a trauma plate or any other known bone fixation device and may further comprise any number of plate holes 106 extending therethrough. FIGS. 5-9 depict a partial cross-sectional view of the target bone 112. Although the bone 112 is shown without any fractures, in practice, the bone 112 may include any number and arrangement of fractures treatable by the bone plate 104.

Figure 2:
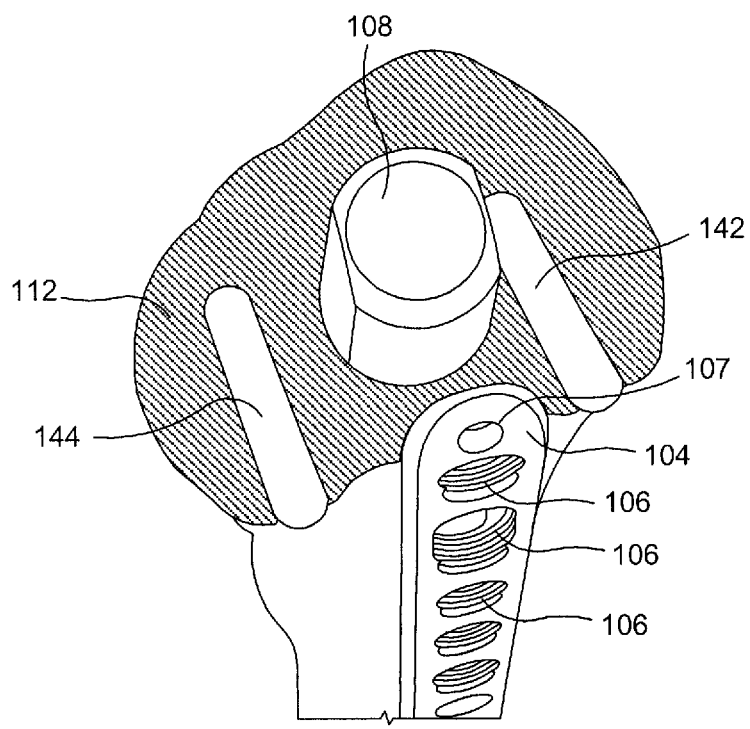
FIG. 2 shows a first partial cross-sectional view of an exemplary method for the system of FIG. 1.

In a first exemplary step, the bone plate 104 is placed against the target bone 112 in a desired orientation and temporarily held in place by, for example, fixation screws inserted into smaller plate holes 107 located on ends thereof. Alternatively, any other means known in the art may be used to temporarily maintain a desired position of the bone plate 104 relative to the bone 112. As shown in FIG. 2, first and second holes 142 and 144 are then drilled into the bone 112 at locations adjacent to a portion of the bone plate 104 to be anchored by the cable tie 102. For example, as described below in this embodiment, the cable tie 102 is locked in place by threading the distal end 128 of the cable tie 102 through a hole 106 in the bone plate 104 and then passing the distal end through a locking mechanism in the head 124 of the cable tie 102. The locking mechanism may, for example, be a projection within a channel of the head 124 which locks in a ratchet fashion with a ribbed portion (e.g., a series of angled teeth) on a face of the cable tie 102. Thus the holes will be drilled in a position corresponding to the hole 106 through which the cable tie is to extend. In another embodiment of the present invention (not shown), the bone plate 104 may be equipped with an integrated locking feature to permit ratcheted locking of the cable tie 102 therewith. The locking feature may be constructed substantially similarly to the head 124 with a projection extending into an opening thereof, the projection engaging a ribbed portion of the cable tie 102 when inserted through the opening. In yet another embodiment, the bone plate 104 may comprise a locking feature (not shown) insertable into a plate hole thereof, the locking feature also permitting ratcheted locking of the cable tie 102 therein in accordance with the system and method discussed earlier.

The drill (not shown) may be guided into the bone 112 under an imaging technique known in the art or by preoperative planning as would be understood by those skilled in the art. The first and second holes 142, 144 are drilled into the bone 112 at an angle substantially perpendicular to a plane of the bone plate 104 separated by a distance selected to achieve a desired separation of the ends of the cable tie 102 passed therethrough around the bone plate 104 so that ends thereof lie substantially adjacent the shaft 108. In a preferred embodiment, the first and second holes 142, 144 are parallel to one another although different angles may be used to bypass a prosthetic implant or other bone fixation element previously implanted in the bone, as those skilled in the art will understand. A guiding instrument 148 is then inserted into the first hole 142 until a distal end thereof engages an end of the first hole 142. The guiding instrument 148 has a diameter substantially equivalent to or smaller than a diameter of the first and second holes 142, 144.

Figure 3:
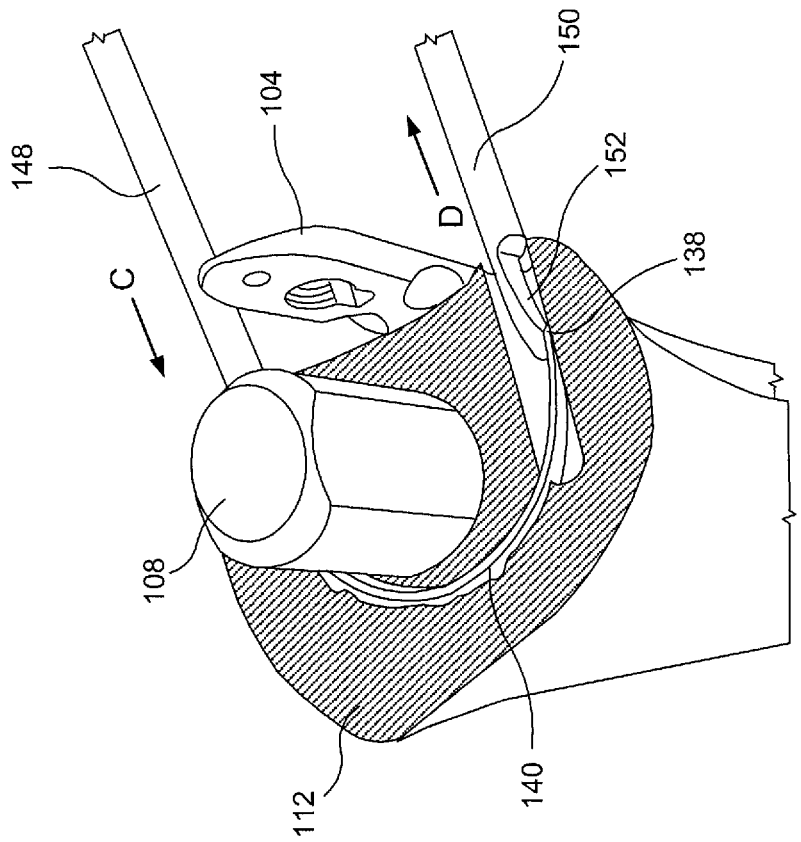
FIG. 3 shows a second partial cross-sectional view of an exemplary method for the system of FIG. 1.
Figure 4:
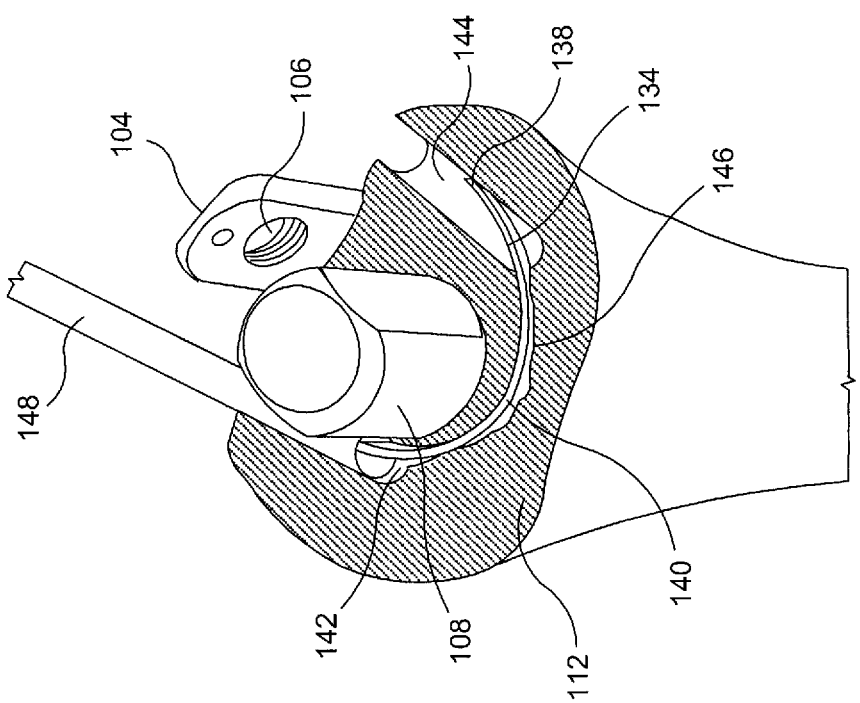
FIG. 4 shows a third partial cross-sectional view of an exemplary method for the system of FIG. 1.
Figure 5:
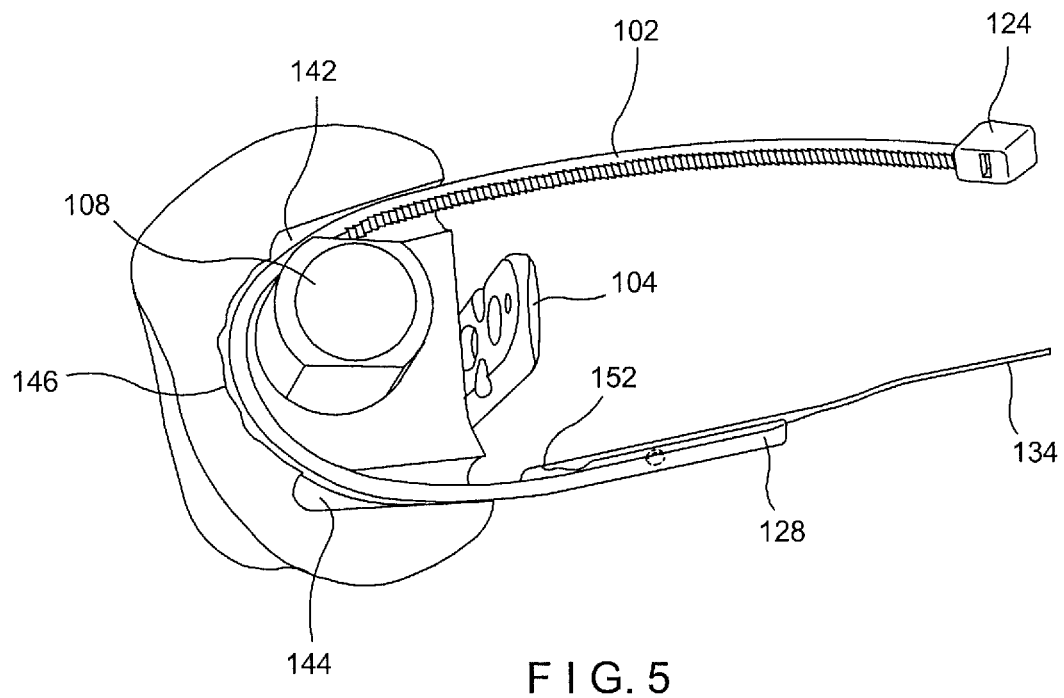
FIG. 5 shows a fourth partial cross-sectional view of an exemplary method for the system of FIG. 1.
Figure 6:
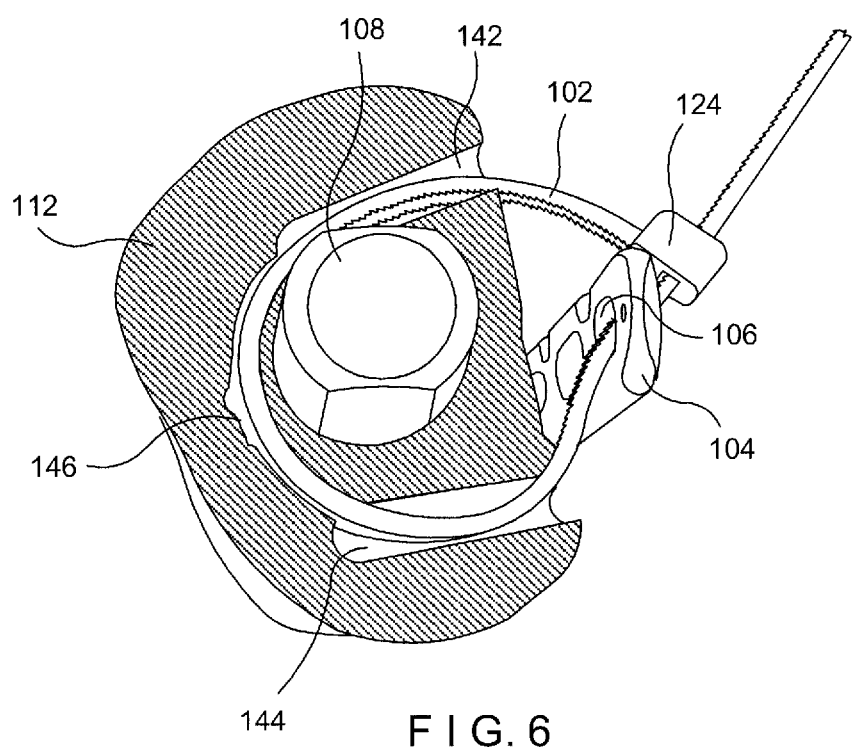
FIG. 6 shows a fifth partial cross-sectional view of an exemplary method for the system of FIG. 1.

As shown in FIG. 3, the guide strip 134 is then advanced out of the guiding instrument 148. As noted earlier, the guide strip 134 is formed of a shape-memory material and will thus automatically assume a memorized shape once confining forces are removed therefrom. Insertion into the guiding instrument 148 straightens the guide strip 134. Accordingly, as the guide strip 134 exits the guiding instrument 148, the second end 138 follows a path dictated by the shape-memorized curve 140. As noted earlier, a curvature of the curve 140 is selected to permit the second end 138 to mate with the second hole 144. By applying a stepped force to the first end 136, the sharpened second end 138 of the guide strip 134 penetrates the bone 112 in a direction extending around the shaft 108 to open into the second hole 144, defining a third curved hole 146 between the first and second holes 142, 144.

A catching instrument 150 is then inserted into the second hole 144 so that a hook 152 formed on a distal end thereof engages the second end 138 of the guide strip 134. A force D is then applied to the catching instrument 150 in conjunction with a force C being applied to the guiding instrument 148 to guide the guide strip 134 completely through the first, second and third holes 142, 144, 146. As noted earlier, a first end 136 of the guide strip 134 is attached to a distal end 128 of the cable tie 102. Thus, the cable tie 102 follows the path of the guide strip 134 through the first, second and third openings 142, 144, 146. The catching instrument 150 is an optional component of the system 100 and, in an alternate embodiment, the guide strip 134 may be traversed through the first, second and third openings 142, 144, 146 solely by applying the force C to the guiding instrument 148. The cable tie 102 is advanced to the position shown in FIG. 4. The free distal end 128 is then disengaged from the guide strip 134 and is woven through a first one of the plate holes 106 and subsequently through the head 124 of the cable tie 102. The cable tie 102 can then be tightened so the head 124 lies adjacent the opening 106 to lock a position of the bone plate 104 against the bone 112. If desired, additional cable ties 102 may be inserted in the bone 112 in accordance with the procedure outlined above.

Various modifications may be made to the system 100 without deviating from the spirit and scope of the present invention. For example, the cable tie 102 may be replaced with a standard cerclage wire, a strap, a retainer or another wire securement mechanism known in the art.

Figure 7:
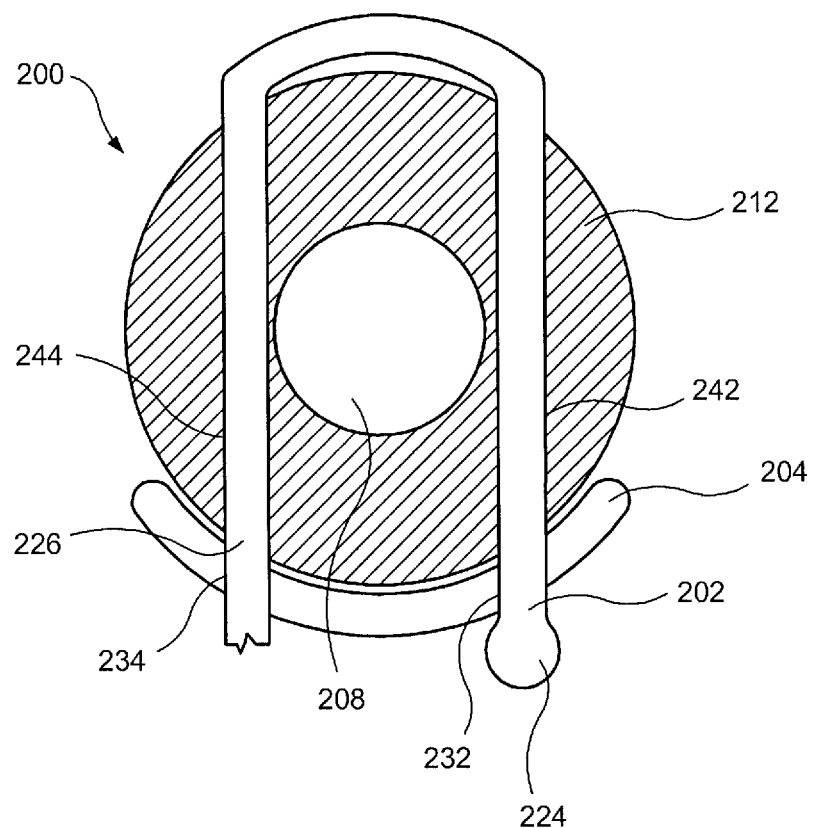
FIG. 7 shows a partial cross-sectional view of a system according to a fifth embodiment of the present invention.

FIG. 7 depicts a system 200 according to another embodiment of the present invention. The system 200 is directed to the fixation of a peri-prosthetic fracture of a bone 212. The system 200 is formed substantially similarly as the system 100 with the exception of the depth of first and second predrilled holes 242 and 244. Specifically, the predrilled holes 242, 244 of system 200 extend completely through the bone 212 along opposite sides of a bone implant 208. The first and second predrilled holes 242, 244 are parallel to one another and are equidistant from the bone implant 208 in order to provide an equal force distribution to the bone 212, as those skilled in the art will understand.

In accordance with an exemplary method for the system 200, a bone plate 204 is first positioned so that first and second plate holes 232, 234 thereof are aligned with the predrilled holes 242, 244. A free distal end (not shown) of a cable 202 is inserted through the first plate hole 232 extending through the bone plate 204, through the first opening 242 extending through the bone 212 and out of an end thereof. The free distal end (not shown) is then inserted into the second opening 244 and advanced therethrough to exit out of the second plate hole 234 aligned therewith. The free end of the cable tie 202 is then inserted through a head 224 of the cable tie 202 so that locking features (not shown) formed on a shaft 226 engage locking features formed within the head 224, as described in greater detail earlier. The cable tie 202 is then tightened to lock the bone plate 204 against an outer periphery of the bone 212 and bone plate 204.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. An apparatus for leading a cerclage member along a desired path through a portion of bone, comprising:
    a guide strip extending from a proximal end to a sharpened distal end, at least a portion of the guide strip being biased to assume a shape corresponding to a portion of a desired path along which the cerclage member is to pass through a portion of bone; and
    a delivery cannula including a lumen sized to slidably receive the guide strip therein, the cannula maintaining the guide strip in a substantially straight configuration until the guide strip is extended distally out of the lumen.

2. The apparatus of claim 1, further comprising a coupling at the proximal end of the guide strip for temporarily attaching the proximal end of the guide strip to a cerclage member having a head and an elongated shaft extending therefrom.

3. The apparatus of claim 1, wherein the guide strip is formed of a shape-memory material.

4. The apparatus of claim 1, further comprising a hook configured to latch onto the sharpened distal end of the guide strip to guide the guide strip through the bone.

5. A method for coupling a bone fixation member to a target portion of bone, comprising: drilling first and second holes substantially parallel to one another through target portions of bone on opposite sides of a site at which the bone fixation member is to be coupled; inserting a delivery cannula adjacent into the first hole, the delivery cannula including a lumen sized to slidably receive a guide strip therein, the guide strip extending from a proximal end to a sharpened distal end, at least a portion of the guide strip being biased to assume a shape corresponding to a desired path along which a cerclage member is to pass through the target portion of bone from the first hole to the second hole, the delivery cannula maintaining the guide strip in a substantially straight configuration; advancing the guide strip distally from the delivery cannula so that the guide strip assumes the biased shape and forms a pathway through the bone substantially along the desired path to enter the second hole; and passing a cerclage member through the first and second holes and along the pathway therebetween and around the bone fixation member to secure the bone fixation member to the bone.

6. The method of claim 5, further comprising the step of securing the proximal end of the guide strip to the cerclage member to pass the cerclage member passed through the first hole, along the pathway into the second hole and out of the second hole around the bone fixation member.

7. The method of claim 6, further comprising the step of tensioning and locking the cerclage member around the bone fixation member.

8. The method of claim 5, wherein the first and second holes are drilled completely through the bone.

9. The method of claim 5, further comprising the step of advancing the guide strip and cerclage member through a bone fixation element to secure the bone fixation element to an outer periphery of the bone.

10. The method of claim 5, wherein the first and second holes are drilled into the bone by a depth smaller than a depth of the bone at the target portions.

11. The method of claim 6, further comprising the step of guiding the guide strip through the bone by inserting a hook into the second hole to latch onto the sharpened distal end of the guide strip.

12. A system for leading a cerclage member along a desired path through a portion of bone, comprising:
    a guide strip extending from a proximal end to a sharpened distal end, at least a portion of the guide strip being biased to assume a shape corresponding to a portion of a desired path along which the cerclage member is to pass through a portion of bone;
    a cerclage member connected to the proximal end of the guide strip via a coupling, the cerclage member having a head and an elongated shaft extending therefrom; and
    a delivery cannula including a lumen sized to slidably receive the guide strip therein, the cannula maintaining the guide strip in a substantially straight configuration until the guide strip is extended distally out of the lumen.

13. The system of claim 12, wherein the shaft of the cerclage member is configured to lockingly engage the head.

14. The system of claim 12, wherein the guide strip is formed of a shape-memory material.

15. The system of claim 12, further comprising a hook configured to latch onto the sharpened distal end of the guide strip to guide the guide strip through the bone.

\* \* \* \* \*